United States Patent [19]

Lange et al.

[11] Patent Number: 5,629,448

[45] Date of Patent: May 13, 1997

[54] ALCOHOL MODIFIED PROCESS FOR PREPARING BIS-SUBSTITUTED PHENOLIC AMIDES

[75] Inventors: Richard M. Lange, Euclid; Mark R. Baker, Lyndhurst; Stephen H. Stoldt, Concord Township, all of Ohio

[73] Assignee: The Lubrizol Corporation, Wickliffe, Ohio

[21] Appl. No.: 721,810

[22] Filed: Sep. 27, 1996

[51] Int. Cl.$^6$ .................................................. C07C 231/02
[52] U.S. Cl. ............................................................ 564/134
[58] Field of Search ................................................ 564/134

[56] References Cited

U.S. PATENT DOCUMENTS

| 3,966,807 | 6/1976 | Elliott et al. | 260/559 |
| 4,051,049 | 9/1977 | Elliott et al. | 252/51.5 |
| 5,281,346 | 1/1994 | Adams et al. | 252/38 |
| 5,336,278 | 8/1994 | Adams et al. | 44/419 |
| 5,356,546 | 10/1994 | Blystone et al. | 252/35 |
| 5,441,653 | 8/1995 | Cleveland et al. | 252/34 |
| 5,458,793 | 10/1995 | Adams et al. | 252/47 |

*Primary Examiner*—Peter O'Sullivan
*Attorney, Agent, or Firm*—John H. Engelmann; Frederick D. Hunter

[57] ABSTRACT

A process for preparing an amide of a bis (hydrocarbyl substituted hydroxyaryl) acetic acid by reacting a lactone produced in the reaction between the glyoxylic acid and phenol with a polyamine in the presence of an alcohol solvent is disclosed.

13 Claims, No Drawings

ALCOHOL MODIFIED PROCESS FOR PREPARING BIS-SUBSTITUTED PHENOLIC AMIDES

BACKGROUND OF THE INVENTION

This invention relates to a process for preparing bis-substituted phenolic amides. More specifically, the process involves the condensation of an alkyl substituted phenol with glyoxylic acid to form a lactone, and the subsequent reaction of the lactone with an amine to form an amide.

U.S. Pat. No. 3,966,807 discloses amides of bis-(phenol substituted)-carboxylic acids and a process for preparing them. In one embodiment, the process involves condensation of an alkyl substituted phenol with an acid such as glyoxylic acid to form a lactone followed by reaction of the lactone with an amine. More particularly, the process disclosed in U.S. Pat. No. 3,966,807 involves heating the co-reactants together either without solvent, or in an inert solvent, such as xylene, toluene or mineral oil.

U.S. Pat. No. 4,051,049 is a divisional application having the same parent as U.S. Pat. No. 3,966,807. The U.S. Pat. No. 4,051,049 discloses the same process for the production of the amide derivatives as that disclosed in U.S. Pat. No. 3,966,807. The reactants are either heated together without solvent, or in the presence of an inert solvent such as xylene, toluene or mineral oil.

U.S. Pat. No. 5,336,278 discloses a fuel composition which includes an amide based on a bis-(phenol substituted)-carboxylic acid. The amide is formed by first condensing a substituted phenol with glyoxylic acid, and thereafter condensing the reaction product with an amine. The reactions with the amine are conducted, either without solvent, or in the presence of an inert solvent such as toluene or xylene.

SUMMARY OF THE INVENTION

A process for preparing a compound of the formula:

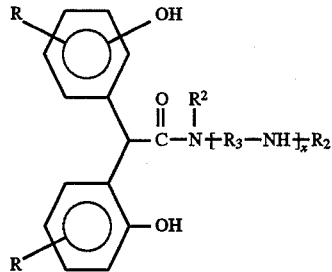

wherein R is a hydrocarbyl group containing 4 to 120 carbon atoms, each $R_2$ is independently a hydrogen or an alkyl group containing 1 to 28 carbon atoms, $R_3$ is an alkylene group containing 2 to 10 carbon atoms, and x is 1 to 5, which comprises the steps of:

I) mixing (A) a lactone of formula:

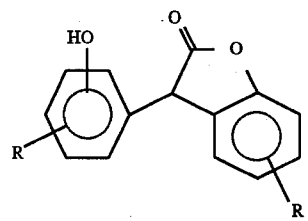

wherein R is a hydrocarbyl group containing 4 to 120 carbon atoms, with (B) a polyamine of the formula:

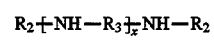

where each $R_2$ independently is hydrogen or an alkyl group containing 1 to 28 carbon atoms, $R_3$ is an alkylene group containing 2 to 10 carbon atoms, and x is 1 to 5, and (C) an alcohol selected from the group consisting of saturated aliphatic alcohols containing 2 to 10 carbon atoms; and polyether alcohols of the following formula:

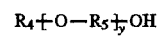

where $R_4$ is a hydrocarbyl group containing from 1 to 30 carbon atoms and $R_5$ is a 3 to 6 carbon alkylene group, and y is between 1 and 30;

II) heating the mixture to a temperature between 60° and 180° C. to form the compound is disclosed.

DETAILED DESCRIPTION OF THE INVENTION

The term "hydrocarbyl" is used herein to include:

(1) hydrocarbyl groups, that is, aliphatic (e.g., alkyl or alkenyl), alicyclic (e.g., cycloalkyl, cycloalkenyl), aromatic, aliphatic- and alicyclic- substituted aromatic groups and the like as well as cyclic groups wherein the ring is completed through another portion of the molecule (that is, any two indicated groups may together form an alicyclic group);

(2) substituted hydrocarbyl groups, that is, those groups containing non-hydrocarbon groups which, in the context of this invention, do not alter the predominantly hydrocarbyl nature of the hydrocarbyl group; those skilled in the art will be aware of such groups, examples of which include ether, oxo, halo (e.g., chloro and fluoro), alkoxyl, mercapto, alkylthio, nitro, nitroso, sulfoxy, etc.; and (3) hetero groups, that is, groups which, while having predominantly hydrocarbyl character within the context of this invention, contain other than carbon in a ring or chain otherwise composed of carbon atoms. Suitable heteroatoms will be apparent to those of skill in the art and include, for example, sulfur, oxygen, nitrogen and such substituents as pyridyl, furanyl, thiophenyl, imidazolyl, etc.

In general, no more than about three nonhydrocarbon groups or heteroatoms and preferably no more than one, will be present for each ten carbon atoms in a hydrocarbyl group. Typically, there will be no such groups or heteroatoms in a hydrocarbyl group and it will, therefore, be purely hydrocarbyl.

The hydrocarbyl groups are preferably free from acetylenic unsaturation; ethylenic unsaturation, when present will generally be such that there is no more than one ethylenic linkage present for every ten carbon-to-carbon bonds. The hydrocarbyl groups are often completely saturated and therefore contain no ethylenic unsaturation.

The present invention provides a process for producing an amide by reaction of (B) a polyamine of the formula:

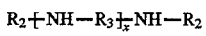

where $R_2$ is hydrogen or an alkyl group containing 1 to 28 carbon atoms, $R_3$ is an alkylene group containing 2 to 10 carbon atoms, and x is 1 to 5, and with (A) a lactone of the following structure:

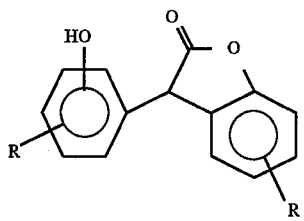

wherein R is a hydrocarbyl group containing 4 to 120 carbon atoms.

The lactone may be formed by methods known to those skilled in the art. For example, the lactone may be formed by condensing glyoxylic acid with a hydrocarbyl substituted phenol. Such methods are disclosed in U.S. Pat. Nos. 3,966,807, 4,051,049 and 5,336,278. These methods employ a condensation reaction in which a hydrocarbyl substituted phenol of the following structure:

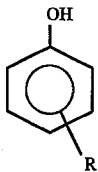

where R is a hydrocarbyl group containing between 4 and 120 carbon atoms is condensed with glyoxylic acid, here shown as the hydrate:

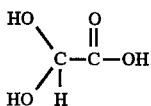

Other methods, known to those skilled in the art, of synthesizing the lactone may be used.

The polyamines which may be used in the reaction include alkylene polyamines of the formula:

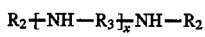

where $R_2$ is hydrogen or an alkyl group containing 1 to 28 carbon atoms, $R_3$ is an alkylene group containing 2 to 10 carbon atoms, and x is 1 to 5. Ethylene polyamines, wherein $R_3$ is a 2 carbon ethylene group are preferred. Polyamines wherein $R_2$ is hydrogen are preferred. In a particularly preferred embodiment the polyamine is diethylenetriamine, that is, $R_2$ is hydrogen, $R_3$ is ethylene, and x is 2. In addition, more highly condensed alkylene polyamines including molecules with branches and cyclic structures such as piperazine rings may be used.

There are several related problems that can arise in carrying out this reaction. The first involves getting good contact between the polyamine and the alkylphenolic lactones described. The polyamines used in this reaction are polar molecules and have low solubility in either those phenolic lactones that contain higher alkyl groups on their aromatic rings, or in the usual non-polar solvents which have been disclosed in the prior art for carrying out the condensations. If the polyamine does not fully dissolve in the reaction mixture a two phase mixture results. In such a two phase system the polyamine, although present, is less available for reaction with the lactone, resulting in lower yields of the desired amide. As a result there is often a significant amount of unreacted, residual polyamine contaminating the product, which can cause considerable corrosion problems, as well as producing undesirable precipitates on storage.

Several different amidic products can result when using a polyamine that contains within its structure multiple reactive amine sites. For example, a polyamine such as diethylenetriamine (DETA) or triethylenetetramine (TETA) contains two terminal primary amines in addition to internal, reactive secondary amines, and all of the amine sites in the molecule may be equally available for condensation with the alkylphenolic lactones. At least two major amidic products may be formed when polyamines such as DETA or TETA are brought into contact with a phenolic lactone of the type described in this disclosure, the first being a mono-amide of the structure represented by

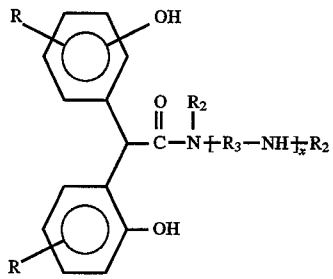

wherein R is a hydrocarbyl group containing 4 to 120 carbon atoms, $R_2$ is hydrogen or an alkyl group containing 1 to 28 carbon atoms, $R_3$ is an alkylene group containing 2 to 10 carbon atoms, and x is 1 to 5.

The second major product can also be a bis-amide of structure (depending on how the reactants are coprocessed):

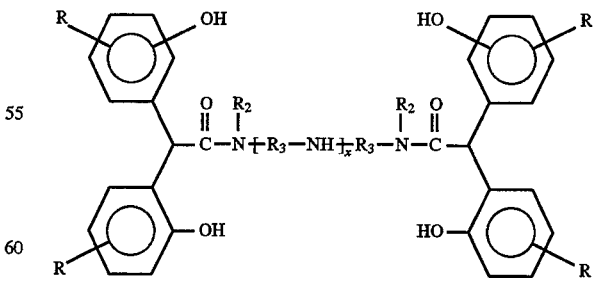

wherein R, $R_2$, $R_3$ are as above.

The problems of polyamine contact and miscibility with the lactone becomes particularly important when trying to make a completely mono-amide product. Once a molecule of polyamine has reacted with a molecule of lactone, the polyamine is preferentially solubilized into the relatively nonpolar reaction mixture as the mono-amide, and the other amine sites it carries become much more available for condensation with other molecules of lactone. The result is an increase in bis- (and higher) amide byproducts. When this happens, the amount of lactone in the reaction mixture quickly becomes depleted, and the product mixture contains not only high levels of the undesired bis-amide, but also considerable unreacted polyamine.

We have found that the use of an alcohol solvent results in higher yields of the monoamide, a smaller amount of the undesirable bis-amide, and leaves very little of the potentially harmful free polyamine in the final product. Generally, heating a lactone with an alcohol results in the formation of an ester. Surprisingly, the phenolic lactones described prove to be unexpectedly resistant to normal ring-opening and ester formation in the presence of alcohols. Two types of alcohols may be used as the solvent. The first is an aliphatic alcohol containing between 2–10 carbon atoms, preferably 4–10 carbon atoms, and most preferably 6–10 carbon atoms. Examples of suitable alcohols include decanol, octanol, 2-ethylhexanol, hexanol, pentanol, butanol, n-propanol, 2-propanol, and ethanol. The second type of alcohol is a polyether alcohol:

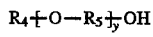

where $R_4$ is a hydrocarbyl group containing From 1 to 30 carbon atoms and $R_5$ is a 2 to 8, preferably 2 to 6, carbon alkylene group, and y is between 1 and 30. Non-limiting examples of suitable polyether alcohols include 2-butoxyethanol, 2-octyloxyethanol, 2-butoxypropanol, 2-(2-butoxy-propoxy)-ethanol, and 2-(lauryloxyethoxyethoxy)-ethanol. Either the polyether alcohol or the aliphatic alcohol may be used alone, or in combination with an inert, non-polar, solvent such as toluene or xylene.

The Reaction

The reaction is conducted in a solvent containing a 8 to 10 carbon saturated aliphatic alcohol. The portion of the alcohol by weight in the total reaction mixture may vary from about 5 to about 35 percent. The polyamine and the lactone are mixed with the solvent and heated to a temperature From 60° to 180° C. Heating and stirring is continued, until the reaction is complete. The progress of the reaction may be followed by infrared spectroscopy. The lactone carbonyl group (CO) has a characteristic absorbance in the infrared (1785 $cm^{-1}$). The amide formed in the reaction also has a characteristic carbonyl absorbance in the infrared (1645 $cm^{-1}$) which is distinguishable from that of the lactone. By withdrawing samples during the reaction, and subjecting them to infrared analysis one can estimate the relative amounts of lactone and amide in the reaction mixture. When the characteristic lactone absorbance has disappeared, the reaction is considered to be complete, whereupon the reaction mixture is cooled to give the final product. The alcohol need not be driven out of the reaction mixture. Optionally, one may wish to have a solvent free product, in which case one may drive off the alcohol by heating the product, sparging with an inert gas, or subjecting the reaction mixture to vacuum and heat. Methods of removing alcohol solvents or mixtures of alcohols and inert solvents are known to those skilled in the art.

Using the low polarity solvents disclosed in the prior art, it is found that there is about 1% by weight free polyamine in the final reaction product. Since the polyamine is a low molecular weight molecule, this relatively small weight percentage of free polyamine corresponds to approximately 27%, on a molar basis, of the polyamine starting material.

EXAMPLE 1

Two thousand (2000) grams of a polyisobutenyl phenol (Mw 1000) (2 moles) was mixed with 148 grams of a 50% aqueous solution of glyoxylic acid (1.0 moles). The mixture was heated to 120° C. degrees for 4 hours. During this time 110 g of water were collected in a Dean-Stark trap. The product was filtered through 200 grams of diatomaceous earth to give 1895 grams of the lactone product. Approximately 143 grams of material were lost in the filtration process.

EXAMPLE 2

13.6 grams of diethylenetriamine (0.15 moles) and 126 grams of a $C_8$ to $C_{10}$, predominantly C9 aromatic solvent with a boiling range of 152°–168° C. were added to 362 grams of the reaction mixture produced in EXAMPLE 1 (containing approximately 0.18 moles of the lactone). The mixture was heated to 120° C. and held at that temperature for 5 hours. The reaction mixture was filtered through 50 grams of diatomaceous earth to yield 482.6 grams of product having a free polyamine level of 1.02% ( 27.6 mole % of the charged polyamine).

EXAMPLE 3

13.6 grams of diethylenetriamine (DETA) (0.13 moles) and 126 grams of polyether alcohol of Mw 900 formed by propoxylating a $C_{14}/C_{16}$ alcohol mixture, were added to 362 grams of the reaction mixture produced in EXAMPLE 1 (containing approximately 0.18 moles of the lactone). The mixture was heated to 120° C. and held at that temperature for 5 hours. The reaction mixture was filtered through 50 grams of diatomaceous earth to yield 482.6 grams of product having a free polyamine level of 0.71% by weight (19.6% of the charged polyamine on a molar basis).

EXAMPLES 4–6

The method of Example 2 was repeated using 13.6 grams of diethylenetriamine (DETA), 362 grams of the product of Example 1, and various alcohols and alcohol mixtures, as set forth in Table 1below. The beneficial effect of various alcohols on both the amine conversion and residual free amine content in the final products is described for each example.

TABLE 1

| Example | Solvent | Free DETA in Product, wt % | DETA Conversion, % |
| --- | --- | --- | --- |
| 2 | C8—C10 aromatic hydrocarbon | 1.02 | 72.4 |
| 3 | 900 molecular wt. polyether alcohol | 0.71 | 80.4 |
| 4 | isopropanol | 0.62 | 82.1 |
| 5 | isobutyl/isoamyl alcohol mixture | 0.54 | 85.8 |
| 6 | 2-ethylhexanol | 0.31 | 91.6 |

What is claimed is:

1. A process for preparing a compound of the formula:

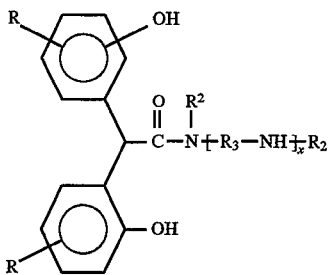

wherein R is a hydrocarbyl group containing 4 to 120 carbon atoms, each $R_2$ is independently a hydrogen or an alkyl group containing 1 to 28 carbon atoms, $R_3$ is an alkylene group containing 2 to 10 carbon atoms, and x is 1 to 5, which comprise the steps of:

I) mixing
  (A) a lactone of formula:

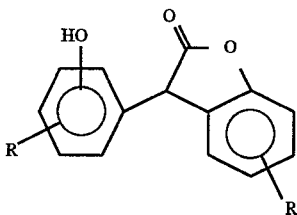

wherein R is a hydrocarbyl group containing 4 to 120 carbon atoms, with
  (B) a polyamine of the formula:

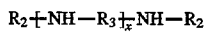

wherein $R_2$ is hydrogen or an alkyl group containing 1 to 28 carbon atoms, $R_3$ is an alkylene group containing 2 to 10 carbon atoms, and x is 1 to 5, and
  (C) an alcohol selected from the group consisting of saturated aliphatic alcohols containing 2 to 10 carbon atoms; and polyether alcohols of the following formula:

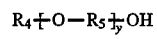

where $R_4$ is a hydrocarbyl group containing from 1 to 30 carbon atoms and $R_5$ is a 2 to 8 carbon alkylene group, and y is between 1 and 30;

II) heating the mixture to a temperature between 60° and 180° C. to form the compound.

2. A process according to claim 1 wherein the aliphatic alcohol contains 4 to 10 carbon atoms.

3. A process according to claim 1 wherein the aliphatic alcohol contains 6 to 10 carbon atoms.

4. A process according to claim 1 wherein the aliphatic alcohol contains 8 to 10 carbon atoms.

5. A process according to claim 1 wherein the aliphatic alcohol is selected from the group consisting of butyl alcohol, amyl alcohol, and 2-ethylhexanol.

6. A process according to claim 1 wherein the aliphatic alcohol is 2-ethylhexanol.

7. A process according to claim 1 wherein the alcohol is a polyether alcohol of the fomula:

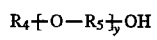

where $R_4$ is a hydrocarbyl group containing from 1 to 30 carbon atoms and $R_5$ is a 2 to 8 carbon alkylene group.

8. A process according to claim 1 wherein the $R_3$ of the polyamine contains 2 carbon atoms.

9. A process according to claim 1 wherein the polyamine is diethylenetriamine.

10. A process according to claim 1 wherein the polyamine is triethylenetetramine.

11. A process according to claim 7 wherein y is 2.

12. A process according to claim 8 wherein the aliphatic alcohol is selected from the group consisting of butyl alcohol, amyl alcohol, and 2-ethylhexanol.

13. A process according to claim 12 wherein the aliphatic alcohol is 2-ethylhexanol.

* * * * *